United States Patent [19]

Prince

[11] Patent Number: 4,981,867
[45] Date of Patent: Jan. 1, 1991

[54] TREATMENT OF TREMOR USING COMPOUNDS THAT DEPRESS CALCIUM CURRENTS IN THALAMIC AND OTHER CENTRAL NERVOUS SYSTEM NEURONS

[75] Inventor: David A. Prince, Portola Valley, Calif.

[73] Assignee: The Board of Trustees of the Leland Stanford Junior University, Stanford, Calif.

[21] Appl. No.: 447,674

[22] Filed: Dec. 8, 1989

[51] Int. Cl.$^5$ ............................................. A61K 31/40
[52] U.S. Cl. ................................................... 514/423
[58] Field of Search ........................................ 514/423

[56] References Cited

PUBLICATIONS

Sinton et al., "The Effectiveness of Different Isomers of Octanol as Blockers of Harmaline-Induced Tremor," *European Journal of Physiology* (1989) 414:31–16.
DeLong, "Possible Involvement of Central Pacemakers in Clinical Disorders of Movement," *Fed. Proc.* (1978) 37:2171–2175.
Coulter et al., "Specific Petit Mal Anticonvulsants Reduce Calcium Currents in Thalamic Neurons," *Neuroscience Letters* (1989) 98:74–78.
Coulter et al., "Calcium Currents in Rat Thalamocortical Relay Neurons: Kinetic Properties of the Transient, Low–Threshold Current," *Journal of Physiology* (1989) 414:587–604.
Coulter et al., "Characterization of Ethosuximide Reduction in Low–Threshold Calcium Current," *Annals of Neurology* (1989) 25:582–593.

Primary Examiner—Stanley J. Friedman
Attorney, Agent, or Firm—Richard L. Neeley

[57] ABSTRACT

A method of treating tremor in mammals, comprising administering to a mammal susceptible to tremor an effective amount of a compound that depresses calcium current in thalamic neurons. Succinimides are particularly effective.

12 Claims, No Drawings

TREATMENT OF TREMOR USING COMPOUNDS THAT DEPRESS CALCIUM CURRENTS IN THALAMIC AND OTHER CENTRAL NERVOUS SYSTEM NEURONS

INTRODUCTION

1. Technical Field

The present invention is directed to the treatment of tremor, particularly tremor associated with Parkinson's disease, multiple sclerosis, and other cerebellar disorders.

2. Background

Tremor is a common medical symptom consisting of a rhythmic oscillation of a part of the body around a fixed point. Tremors can involve the distal parts of limbs; the head, tongue, or jaw; or (rarely) the trunk. The mechanisms by which tremors are generated have been poorly understood; however, it is long been thought that tremors are brought about by interactions of nerve cells in complex, incompletely understood circuits within the brain.

Tremors are subdivided clinically in a number of ways according to distribution, frequency, amplitude, and/or relationship to volitional movement. One type of tremor that is commonly recognized is known as tremor at rest. This is a coarse tremor with an average rate of 4 to 5 beats per second and is a frequent feature of Parkinson's disease. This type of tremor gains its name from its relationship to volitional movement. This tremor typically occurs when a limb is at rest; willed movement temporarily surpresses the tremor. In some cases, the tremor is constant; in others it varies from time to time and may extend from one group of muscles to another as the disease progresses.

Another type of tremor, termed action tremor or intention tremor, is associated with cerebellar disorders. For example, patients with multiple sclerosis, which frequently involves the cerebellum and its connections, sometimes develop a coarse tremor which is brought on by activity and absent at rest. Other cerebellar disorders, such as the inherited cerebellar degenerations, also may have action tremor as a major symptom.

Another, tremor brought out by activity is known as essential (or essential-familial) tremor. This tremor sometimes begins in childhood but usually occurs later and persists through adult life, often affecting several members of a family (hence its name). It is known that essential-familial tremors can be suppressed by primidone or CNS-active $\beta$-adrenergic blocking agents, such as propranolol.

A number of other types of tremors also exist, including physiologic tremor (typically associated with excitement and other hyperandrenergic states; stage fright is a typical example). Numerous reviews of the various tremor states exist, such as can be found in Chapter 15 (entitled "Paralysis and Other Disorders of Movement") of Harrison's *Principles of Internal Medicine* 11th Edition, Brownwald et al., Eds., McGraw-Hill Book Company, New York, 1987.

Unfortunately, many patients with tremor are resistant to current therapies. The tremor of patients with Parkinson's disease may be only partially responsive to the actions of trihexyphenidyl and related anticholinergic drugs or to dopamine agonists. Additionally, unexceptable central nervous system side effects, including confusion and hallucinations, are sometimes associated with current Parkinson's disease treatments. Treatments of the tremor of cerebellar disease are also generally ineffective. Accordingly, there remains a need for improved methods of treating tremor that are specific for the underlying physiological mechanisms.

The present inventor has been working recently in an area previously believed to be unrelated to tremor, namely in fundamental research into a particular calcium current found in neurons of the mammaliam thalamus, called the transient calcium current or "T current." See, for example, Coulter et al., *J. Physiology* (1989) 414: 587–604. Investigations have centered on drugs which might suppress the T current because of experimental evidence that this current is important in the generation of normal rhythms seen in the electoencephalogram (e.g., the normal "sleep spindle"), as well as abnormal rhythms, such as the 3-per-second spike-wave discharge that occurs in petit mal epilepsy. Some of this work has been published and indicates that anticonvulsants known to reduce the effects of petit mal epilepsy apparently act by reducing transient calcium currents in thalamic neurons. See, for example, Coulter et al., *Neuroscience Letters* (1989) 98: 74–78 and Coulter et al., *Annal of Neurology* (1989) 25: 582–593. Also see Sinton et al., *European Journal of Physiology, Pflugers Arch.* (1989) 414: 31–36, in which toxic high molecular weight alcohol was used to block drug-induced tremor in rats.

However, prior to the present invention, there has been no association between transient calcium currents in thalamic or other central nervous system neurons and treatment of tremor in human patients.

SUMMARY OF THE INVENTION

Accordingly, it is an object of the present invention to provide a new method for treating tremor, particularly tremor associated with Parkinson's disease, essential tremor, and cerebellar disease.

This and other objects of the invention as will hereinafter become apparent have been accomplished by providing a method for reducing tremor in mammals, comprising administering to a mammal susceptible to tremor an effective amount of a compound that depresses transient calcuim current in thalamic and other neurons in the mammal. Classes of compounds of particular effectiveness include anticonvulsant succinimides and oxazolidinediones.

DESCRIPTION OF SPECIFIC EMBODIMENTS

The present invention arose in part out of investigations in the laboratory of the inventor which indicated that depression of the transient calcium current in thalamic neurons is the mode of action by which certain anticonvulsants used to treat petit mal epilepsy operate. The present invention also arose out of a realization that Purkinje cells of the cerebellum, neurons in the inferior olive, and most neurons in the thalamus have two important properties in common: they all generate prominent T-currents which can lead to oscillatory behavior, and each is part of a structure that is known to be involved in generation of tremors. This realization, together with information on the mode of action of anticonvulsant succinimides, first described in the laboratories of the inventor, has led to the conclusion that drugs which supress the transient calcium current (T current) in thalamic and other neurons will also be effective for therapy of certain types of tremors in humans and other mammals.

The present invention can be carried out using any compound that depresses the transient calcium current in thalamic neurons. Compounds that depress this current in thalamic neurons are also known to depress the T current in Purkinje cells in the cerebellum and neurons of the inferior olive. Accordingly, indication herein that administration of a compound to a subject depresses the T current in thalamic neurons is indicative of a property that affects other neurons as well. Thus, a compound that depresses the T current in thalamic neurons can be used to treat disorders involving other central nervous system neurons such as those of the cerebellum or inferior olive.

While some such compounds are currently known, new classes of compounds having this property and therefore being useful in reducing tremor can readily be determined by measuring the ability of a compound to depress the transient calcium current. Ability of any compound to suppress calcium currents of thalamic neurons can be determined by a number of techniques, such as the so-called patch-clamp technique described in Hammill et al., *Pfluegers Arch.* (1981) 391: 85–100. Neurons from the ventrobasal complex of guinea pigs or rats are isolated using the technique described in Kay et al., *J. Neurosci. Methods* (1986) 16: 227–238. Cells are isolated using a combination of enzymatic and mechanical dissociation and viewed in a petri dish. Standard patch-clamp techniques are applied, using intracellular and extracellular solutions that block all but calcium currents as described in Coulter et al., *J. Physiol.* (1989) 414: 587–604. Under voltage clamp, selection of appropriate holding and command voltages allows the transient calcium current to be activated in isolation from other currents. Drugs are applied to the clamped neuron from broken micropipettes or using bath perfusion. The effects on the transient calcium current are recorded on magnetic tape and analyzed on line or off line. Appropriate controls, including compounds known to be inactive on the T-current, are employed. These techniques have been published in detail (Coulter et al., *J. Physiol.* (1989) 414: 587–604; Coulter et al., *Neuroscience Letters* (1989) 98: 74–78; Coulter et al., *Ann. Neurol.* (1989) 25: 582–593). Details of an exemplary measurement are set forth in the examples that follow.

In view of the demonstrated ability of certain selective petit mal anti-epileptic drugs to suppress the T current in thalamic neurons, all such compounds should be considered useful in reducing tremor in mammals until shown otherwise. Such compounds include succinimides, oxazolidinediones, and some benzodiazepines. Specific examples of drugs from these classes include ethosuximide, methsuximide, phensuximide, trimethadione, paramethadione, and clonazepam. Hydantoins also suppress the T current, but at levels that may be toxic. A typical hydantoin is phenytoin.

Compounds of the succinimide and oxazolidinedione classes are particularly preferred. Especially preferred are compounds of the formula

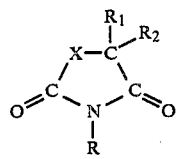

wherein:

R is H or lower alkyl;

$R_1$ and $R_2$ are independently selected from the group consisting of H, lower alkyl, aryl, and aryl lower alkyl; and X is -O- or $-CHR_3-$, wherein $R_3$ is H or lower alkyl; with the proviso that at least one of $R_1$, $R_2$, and $R_3$ is an indicated substituent other than hydrogen. Lower alkyl here and elsewhere preferably means a linear or branched alkyl group containing from 1 to 5 carbon atoms. Aryl groups are preferably carbocyclic or heterocyclic systems containing one or two aromatic rings (when two ring, preferably fused). Examples of suitable aryl rings include benzene, furan, thiophene, pyrrole, pyrazole, triazole, isoxazole, oxazole, thiazole, isothiazole, pyran, pyrone, dioxin, pyridine, pyridizine, purimidine, pyrazine, triazine, indene, benzofuran, isobenzofuran, benzothiofuran, indole, napthalene, coumarin, quinoline. and isoquinoline. Simple aryl groups such as phenyl, napthyl, and single-ring heterocycles are preferred. Phenyl is particularly preferred. Preferred aryl lower alkyl groups are those in which the aryl and lower alkyl substituents have the previously defined meanings. In all cases, normal substituents found on alkyl groups and aromatic rings, such as halogen, amino, hydroxy, and amido groups, can be present and are included within the meaning of alkyl and aryl. However, aryl groups substituted only with hydrogens are preferred.

Certain compounds of the formula indicated above are preferred. When the compound is a succinimide, R is preferably hydrogen or methyl, $R_1$ is preferably hydrogen or methyl, $R_2$ is preferably methyl, ethyl, or phenyl, and $R_3$ is preferably hydrogen. Especially preferred are 2-methyl-2-ethyl succinimide, N-methyl-2-phenyl succinimide, and N,2-dimethyl-2-phenyl succinimide.

When the compound is an oxazolidinedione, R is preferably hydrogen or methyl (especially methyl), $R_1$ is preferably methyl, and $R_2$ is preferably methyl or ethyl. The compounds N,5,5-trimethyloxazolidinedione (trimethadone) and N,5-dimethyl-5-ethyloxazolidinedione (paramethadone) are especially preferred.

Administration can be by any technique designed to cause the active agent to enter the blood stream of the mammal and be circulated to the appropriate brain tissues. Oral administration is particularly preferred and is known for all of the specific classes of drugs mentioned above. Particular blood levels desired for optimum performance will vary depending on the type of drug used and can be determined by direct serum measurements and by the effect of the compound in reducing tremor. Typical initial doses for succinimides range from about 1 to 25 mg/kg, preferably about 2 to about 20 mg of compound per kilogram of mammal. Preferred daily totals are 250 to 1000 mg for ethosuximide and 150 to 1200 mg for methsuximide. For known compounds that have previously been used to treat other disorders, such as epilepsies, initial concentrations can be those concentrations normally used for the other treatment. Adjustments can then be made, upward or downward, depending on the reduction of tremor, the measured serum level, and/or side effects that occur. Considerable variation between treated individuals is likely to occur so that the actual dosage used is best obtained by following the pharmacologic effects on the individual being treated. Dosage information is available from numerous sources, such as Goodman and Gillman's *The Pharmacological Basis of Therapeutics*, 7th Edition, Gillman et al., Eds., McMillan Publishing Company, New York, 1985. Chapter 20 of Goodman and Gillman is specifically directed to drugs effective in the therapy of the epilepsies and includes discussion of a number of the classes of compounds described in this specification.

When new classes of drugs are being investigated for reducing tremor, potentially satisfactory performance is indicted by ability of the compound being tested in the laboratory to reduce the transient calcium current by at least 10%, preferably by at least 25%, preferably without adverse pharmacological effects.

Since tremor is typically a chronic disorder, administration of a compound of the invention will typically occur at regular intervals (e.g., once or more times per day) over extended periods of time, typically at least one week, and generally extending over several years.

The method of the present invention is usually practiced as a treatment to reduce the effects of tremor after onset, but can also be used prophylactically before onset in patients predisposed to tremor, such as Parkinson's patients. The method of the present invention is particularly useful in treating Parkinson's disease, especially with the succinimides, such as ethosuximide, as there appears to be generally useful beneficial effects for multiple Parkinson's symptoms.

The following examples are offered by way of illustration and not by way of limitation.

EXAMPLES

The examples below describe specific techniques used in the measurement of drug effects on transient calcium currents of thalamic neurons. Also see Coulter et al., *Neurosci. Letters* (1989) 98: 74–78; Coulter et al., *Ann. Neurol.* (1989) 25: 582–593; and Coulter et al., *J. Physiol.* (1989) 414: 587–604.

Example 1: Neuron preparation and enzymatic isolation procedure

The somatosensory ventrobasal complex (VB) of the rat was used as a source of thalamic neurons because in rodents this set of nuclei contains a nearly pure population of relay cells; there are less than 1% interneurons (Jones, *The Thalamus* (1985) Plenum Press, New York; Harris et al., *Neuroscience* (1988) 21: 229–236).

All experiments were carried out using cells isolated from 2 to 25 day old Wistar rats. Dissociation methods were modified from those of Kay et al., *J. Neurosci. Methods* (1986) 16: 227–238. Pregnant rats were obtained at 18 days gestation from Simonsen Laboratories (Gilroy, Calif.). Rat pups were anesthetized with pentobarbitone, decapitated, and the brains removed and placed in cold saline (4° C.) for 1 to 2 minutes. The brain was then blocked and sectioned in the coronal plane using a Lancer vibratome (St. Louis, Mo.). Slices (500 $\mu$M) that contained the ventrobasal (VB) complex were dissected by scalpel cuts to isolate the thalamus. VB was identified as a crescent shaped area, demarcated on its lateral and ventral borders by the external medullary lamina, medial lemniscus and reticular nucleus. In the youngest animals, where myelination was less complete, VB was identified by comparing living slices with an atlas made from Nissl stains of comparably aged animals. Thalamic slices were then incubated for 45 to 90 minutes in an oxygenated PIPES buffered saline (see below) containing trypsin (Type XI, 8 mg/10 ml). After enzymatic treatment, the slices were washed in trypsin-free PIPES saline, and VB was isolated with scalpel cuts. Once isolated, each VB section was divided in half, triturated with fire-polished Pasteur pipettes, and plated onto 35 mm plastic petri dishes (Lux tissue culture dishes, Miles Scientific, Naperville, Ill.). Isolated relay neurons were somewhat variable in appearance but a majority had relatively large somata (15–25 $\mu$m) and several thick (2–3 $\mu$m) dendrites extending for up to 80 $\mu$m from the soma. These neurons survived for up to 12 hours following isolation.

Example 2: Preparation of solutions

A PIPES buffered saline was used in all steps prior to recording currents. It consisted of (in mM): NaCl 120, KCl 5, $MgCl_2$ 1, $CaCl_2$ 1, glucose 25, piperazine-N,N'-bis[2-ethanesulfonic acid] (PIPES) 20, and the pH was adjusted to 7.0 with NaOH (Kay et al. *J. Physiol.* (1986) 392: 603–616). For whole cell recording of $Ca^{2+}$ currents the following solutions were used: Intracellular -- Tris $PO_4$ dibasic 110, Tris base 28, ethyleneglycol-bis-($\beta$-aminoethyl ether) N,N,N',N'-tetra-acetic acid (EDTA) 11, $MgCl_2$ 2, $CaCl_2$ 0.5, $Na_2$ ATP 4, pH 7.3; Extracellular -- NaCl 155, KCl 3, $MgCl_2$ 1, $CaCl_2$ 3, tetrodotoxin 0.0005, N-2-hydroxyethylpiperazine-N'-2-ethanesulfonic acid HEPES) 10, and pH adjusted to 7.4 with NaOH. All chemical were obtained from Sigma (St. Louis, Mo.).

The concentration of $Ca^{2+}$ used in these experiments (3 mM) is somewhat higher than that in cerebrospinal fluid or the extracellular space of the brain, where the concentration would be near 2 mM. The increased concentration of divalent cations increases the screening charge (Frankenhauser et al., *J. Physiol.* (1957) 137: 218–244; Hille, *J. General Physiol.* (1968) 51: 221–236, and therefore shifts the voltage dependence of the gating parameters for $Ca^{2+}$ currents. Because $[Ca^{2+}]_o$ used is approximately 1.5 times normal, in the physiological situation the voltage dependence of all kinetic properties would be approximately 3 to 4 mV less negative than recorded.

Example 3: Electrophysiogical Recordings

Isolated relay neurons were voltage-clamped using the whole-cell configuration of the patch clamp (Hammil, Marty, et al., *Pfugers Archiv* (1981) 391: 85–100). Electrodes were pulled from thick-walled borosilicate glass (H15/10/181, Jencons Ltd., Leighton Buzzard, England) on a List L/M-3P-A (Medical Systems, Great Neck, N.Y.) puller using a two step procedure. When filled with intracellular tris-$PO_4$ solution, electrode resistances were 5 to 8 M$\Omega$. An 8 mV liquid junction potential was measured between the intracellular and extracellular solutions (see Hagiwara et al., *J. Physiol.* (1982) 331: 231–252), and this correction was applied post facto to all command potentials. Current recordings were obtained with either the List EPC-7 (Medical Systems) or the Axopatch 1A amplifier (Axon Instruments, Burlingame, Calif.). In either case, series resistance compensation was used to eliminate 90% of the voltage error due to the passage of current through the patch pipette. Access resistance was normally in the range of 6 to 10 M$\Omega$. Inward $Ca^{2+}$ currents were always less than 1 nA with a resulting maximum series resistance error smaller than 1 mV, when compensated by 90%.

A modified P/X substraction technique (based on Bezanilla et al., *J. General Physiol.* (1977) 70: 549–566)

was used to remove interference from linear leak and capacitative currents. Several sealed hyperpolarizing leak pulses were applied from a reduced holding potential (−50 mV) before the holding potential was increased to conditioning potential (normally −100 mV) for 1 s preceding the command step. Stimuli were normally applied at <0.1 Hz. These protocols allowed $Ca^{2+}$ currents to be recorded in relay neurons for up to 75 minutes. $Ca^{2+}$ current records obtained by P/X substraction were indistinguishable from those in experiments where the leak and capacitative currents were obtained by applying the normal stimulation protocol to a neuron bathed in normal extracellular saline with 0.5 mM $CdCl_2$ added to block $Ca^{2+}$ currents.

Voltage clamp control was judged by several criteria, including (1) smooth voltage-dependent current activation, (2) lack of excessive delay in onset of current, and (3) onset and offset kinetics that were dependent on voltage but not on the amplitude of current. Only cells in which adequate clamp conditions were obtained using these criteria were included in kinetic studies. Isopotentiality of neuronal membrane was assured by testing the exporentiality of the capacitative transient (Kay et al., *J. Physiol.* (1987) 392: 603–616).

When drugs were applied using bath perfusion with high flow rates (for example, in obtaining ethosuximide dose-response data), fluctuations in solution level often induced oscillations due to the $R_S$ compensation circuitry. For this reason, $R_S$ compensation was not used in these instances, and the potential $R_S$ error therefore increased to 5mV.

Example 4: Drug concentrations and method of application

All anticonvulsants were applied in concentration ranges which were clinically relevant (i.e., in concentrations which are achieved as free serum levels in epileptic patients medicated with a particular anticonvulsant). For ethosuximide and dimethadione, this concentration range is 280 to 700 μM (40 to 100 μg/ml), (Aicardi, *Epilespy in Children* (1986) Raven, N.Y.; Browne et al., *Neurology* (1975) 25: 515–524) and 5 to 9 mM (700 to 1200 μg/ml) (Booker, "Relation of Plasma Concentration to Seizure Control" in *Antiepileptic Drugs* (1982) Woodbury et al., Eds. Raven, N.Y.; Chamberlain et al., *Neurology* (1965) 8: 106–112), respectively. Drugs were either applied by changing the extracellular bathing medium, or by perfusion onto the cell, produced by applying pressure to the back of drug-containing, broken micropipettes (tip diameter 2 to 4 μm).

Most experiments were performed at room temperature (22° to 24° C.) since survival of isolated cells was prolonged under these conditions. Bath temperature was monitored with a small thermocouple placed in the chamber within 100 μm of the neuron under study.

Example 5: Data storage and analysis

Data were sampled on line in either unsubstrated or leak-subtracted form using a DEC 11-73 based computer equipped with the Cheshire interface (Indec Systems, Sunnyvale, Calif.) running under BASIC-23. Currents and command voltages were also recorded in pulse code modulated form (Neurocorder, Neurodata, N.Y.) and stored on video tape for backup purposes. For kinetic fits to current records, an iterative approach was used in which the parameters were adjusted by means of the analog inputs on the Cheshire interface. This method was found to provide a rapid means of fitting onsets and exponential decays with up to two components. A nonlinear least squares fitting routine (Schreiner, et al., *PC Technical Journal* (1985) 3: 170–181) was used to verify these results in representative traces; the fits obtained by these two methods were not significantly different in the rate constants or amplitudes of the various components.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing tremor in mammals, comprising:
   administering to a mammal susceptible to tremor a tremor-reducing amount of a compound having the formula

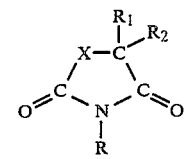

wherein:
R is H or lower alkyl:
$R_1$ and $R_2$ are independently selected from the group consisting of H, lower alkyl, aryl, and aryl lower alkyl; and
X is -O- or -$CHR_3$-, wherein $R_3$ is H or lower alkyl; with the proviso that at least one of $R_1$, $R_2$, and $R_3$ is an indicated substituent other than hydrogen.

2. The method of claim 1, wherein said aryl is a phenyl group.
3. The method of claim 2, wherein X is -$CHR_3$-.
4. The method of claim 3, wherein $R_3$ is H.
5. The method of claim 4, wherein said compound is 2-methyl-2-ethylsuccinimide, N-methyl-2-phenylsuccinimide, or N,2-dimethyl-2-phenylsuccinimide.
6. The method of claim 5, wherein said amount is from about 1 to about 25 mg of said compound per kg of said mammal.
7. The method of claim 5, wherein said administering is by oral ingestion.
8. The method of claim 5, wherein said administering occurs at regular intervals for at least one week.
9. The method of claim 5, wherein said administering occurs after onset of tremor as a treatment.
10. The method of claim 5, wherein said tremor is associated with Parkinson's disease.
11. The method of claim 5, wherein said tremor is essential tremor.
12. The method of claim 5, wherein said tremor is cerebellar in origin.